United States Patent
Xie et al.

(10) Patent No.: US 8,664,611 B2
(45) Date of Patent: Mar. 4, 2014

(54) POSITRON EMISSION TOMOGRAPHY METHOD AND DEVICE WITH APPLICATION ADAPTABILITY

(75) Inventors: Qingguo Xie, Wuhan (CN); Jingjing Liu, Wuhan (CN)

(73) Assignees: Raycan Technology Co., Ltd. (Su Zhou), SND Suzhou (CN); Huazhong University of Science and Technology, Wuhan (CN)

( * ) Notice: Subject to any disclaimer, the term of this patent is extended or adjusted under 35 U.S.C. 154(b) by 0 days.

(21) Appl. No.: 13/703,625

(22) PCT Filed: Jan. 4, 2011

(86) PCT No.: PCT/CN2011/000006
§ 371 (c)(1),
(2), (4) Date: Dec. 11, 2012

(87) PCT Pub. No.: WO2011/157045
PCT Pub. Date: Dec. 22, 2011

(65) Prior Publication Data
US 2013/0087697 A1    Apr. 11, 2013

(30) Foreign Application Priority Data
Jun. 13, 2010   (CN) .......................... 2010 1 0200478

(51) Int. Cl.
*G01T 1/166* (2006.01)
*G12B 13/00* (2006.01)

(52) U.S. Cl.
USPC .................................. 250/363.04; 250/252.1

(58) Field of Classification Search
USPC ........ 250/252.1, 363.03, 363.04, 370.09, 394
See application file for complete search history.

(56) References Cited

U.S. PATENT DOCUMENTS

| | | | |
|---|---|---|---|
| 4,980,552 | A | 12/1990 | Cho et al. |
| 5,825,031 | A | 10/1998 | Wong et al. |
| 5,900,636 | A | 5/1999 | Nellemann et al. |
| 2002/0148970 | A1 | 10/2002 | Wong et al. |
| 2010/0046818 | A1 | 2/2010 | Yamaya et al. |

FOREIGN PATENT DOCUMENTS

| | | |
|---|---|---|
| CN | 101536913 A | 9/2009 |
| CN | 101856236 A | 10/2010 |
| JP | 8-21154 A | 1/1996 |

OTHER PUBLICATIONS

Miles N. Wernick, et al., Emission Tomography: The Fundamentals of PET and SPECT, Elsevier Academic Press, 2004.
Michael E. Phelps, PET Physics, Instrumentation, and Scanners, Springer, 2006.

(Continued)

*Primary Examiner* — Mark R Gaworecki
(74) *Attorney, Agent, or Firm* — Knobbe Martens Olson & Bear LLP

(57) ABSTRACT

A positron emission tomography method and a device with application adaptability. The method includes: step 1, scanning a tested object for obtaining initial activity information of the tested object; step 2, programming and adjusting a detector module based on the result of the initial scan to obtain a new system structure, and rapidly calibrating the new system structure; step 3, performing a scan with the new system structure for obtaining activity information of the tested object; step 4, analyzing the activity information of the tested object obtained at step 3. If quality of the activity information can satisfy requirements of the application, the scan is finished; otherwise programming and adjusting the detector module is repeated, rapid calibration is performed, and the activity information of the tested object is obtained again with the new system structure until the activity information satisfies requirements.

22 Claims, 3 Drawing Sheets

(56) References Cited

OTHER PUBLICATIONS

Craig S Levin, et al., Calculation of positron range and its effect on the fundamental limit of positron emission tomography system spatial resolution, Physics in Medicine and Biology, vol. 44, pp. 781-799, 1999.

F Lamare, et al., Validation of a Monte Carlo simulation of the Philips Allegro/GEMINI PET systems using GATE, Physics in Medicine and Biology, vol. 51, pp. 943-962, 2006.

Brad J. Kemp, et al., NEMA NU 2-2001 performance measurements of an LYSO-based PET/CT system in 2D and 3D acquisition patterns, Journal of Nuclear Medicine, vol. 47, pp. 1960-1967, 2006.

Laforest Richard, et al., Performance evaluation of the microPET-Focus-F120, in IEEE 2004 Nuclear Science Symposium Conference Record, vol. 5, pp. 2965-2969, 2004.

Cristian C Constantinescu, et al., Performance evaluation of an Inveon PET preclinical scanner, Physics in Medicine and Biology, vol. 54, pp. 2885-2899, 2009.

Paul E. Kinahan, et al., X-ray-based attenuation correction for positron emission tomography/computed tomography scanners, Seminars in Nuclear Medicine, vol. 33, pp. 166-179, 2003.

Andrew J. Reader, et al., Advances in PET Image Reconstruction, Clin., pp. 173-190, 2007.

Dewalle-Vignion AS, et al., Thresholding methods for PET imaging: A review, Medicine Nucleaire, vol. 34, No. 2, pp. 119-131, 2010.

National Electrical Manufacturers Association, NEMA Standards Publication NU 2-2007, Performance Measurements of Small Animal Positron Emission Tomographs, 2007.

POSITRON EMISSION TOMOGRAPHY METHOD AND DEVICE WITH APPLICATION ADAPTABILITY

CROSS-REFERENCE TO RELATED APPLICATIONS

The present application is the national phase of International Application No. PCT/CN2011/000006, titled "POSITRON EMISSION TOMOGRAPHY METHOD AND DEVICE WITH APPLICATION ADAPTABILITY", filed on Jan. 4, 2011, which claims the benefit of priority to Chinese patent application No. 201010200478.0 titled "POSITRON EMISSION TOMOGRAPHY METHOD AND DEVICE WITH APPLICATION ADAPTABILITY", filed with the Chinese State Intellectual Property Office on Jun. 13, 2010. The entire disclosure thereof is incorporated herein by reference.

FIELD OF THE INVENTION

The present invention generally relates to a positron emission tomography (hereinafter referred to as PET for short) imaging method and imaging device with application adaptability, which belong to the field of PET.

BACKGROUND OF THE INVENTION

Positron Emission Tomography (hereinafter referred to as PET for short) is a non-invasive imaging method which can non-invasively, quantitatively and dynamically assess the metabolism, biochemical reactions, functional activities and perfusion of various organs of human body. Therefore, PET is used for early diagnosis and analysis of tumors, cardiac diseases and neurological diseases and plays a unique role in the prevention and treatment of serious diseases. During a PET imaging, it is needed to inject a drug marked with radioisotopes into a human body, an animal or an organism under detection. In the tissue of the object under detection, these radioisotopes encounter electrons and annihilate to generate a pair of γ photons. A detector at the periphery of the object under detection receives the γ photons and converts them into electrical signals. A series of processes are performed on these electrical signals, and an activity distribution of the object under detection is obtained by image reconstruction. [Miles N. Wernick, John N. Aarsvold, Emission Tomography: The Fundamentals of PET and SPECT, Elsevier Academic Press, 2004]

PET mainly includes a detector module, an electronics module and an image reconstruction module. The detector module receives and deposits γ photons and converts the γ photons into electrical signals; the electronics module processes and transmits these electrical signals the image reconstruction module processes the signal obtained by the system to obtain an image of activity distribution of the object under detection. After a PET system is installed, the detector module is fixed during a detection process or rotates around a fixed center in a fixed pattern [Michael E. Phelps, PET Physics, Instrumentation, and Scanners, Springer, 2006]. Moreover, for one object under detection, generally only one detection is performed or multiple independent detections are performed, and the layout and performance of the detector module are not adjusted in accordance with the characteristics of the specific object under detection.

Nowadays, animal PET achieves a better performance in spatial resolution, timing resolution, energy resolution, sensitivity, counting rate and so on as compared with PET for human body (hereinafter referred to as "human PET" for short, "PET" also refers to "human PET" unless otherwise indicated). The main reason lies in that, due to the partial volume effect, a better design scheme of the detector module is required for the purpose that the animal PET achieves the same performance as the human PET. If the design scheme of the detector module of the animal PET s used for the human PET, the ratio of the cost of the scintillation crystals between the human PET or the animal PET is proportional to the square of the ratio of the radius of a detection ring. Assuming that the field of view in the vertical axial direction (hereinafter referred to as FOV for short) of the human PET is 60 cm and for the animal PET it is 12 cm, and the axial FOV of the human PET and animal PET is same, the cost of the scintillation crystals for the human PET is at least 25 times as big as that of the animal PET.

The property of spatial resolution is taken as an example to illustrate the difference between the human PET and the animal PET. Spatial resolution is one of the most important performance indexes of PET. The higher spatial resolution means that it is able to detect a smaller lesion. Since the lesion size of an early cancer is commonly small, a PET with higher spatial resolution can improve the detecting rate for the early cancer. In the past, much work has been made to improve the spatial resolution of the PET system. The spatial resolution is mainly limited by the intrinsic spatial resolution of the detector, positron range, non-collinearity and so on [Craig S Levin, Edward J-Hoffman, "Calculation of positron range and its effect on the fundamental limit of positron emission tomography system spatial resolution," Physics in Medicine and Biology, vol. 44, pp. 781-799, 1999]. Currently, for the human PET, the spatial resolution is about 2 mm~10 mm Full Width at Half Maximum (hereinafter referred to as FWHM for short), the FOV in the vertical axial direction is approximately 50~70 cm, the width of the scintillation crystal in the tangential direction is generally about 4 mm~8 mm [F Lamare, A Turzo, Y Bizais, C Cheze Le, Rest, D Visvikis, "Validation of a Monte Carlo simulation of the Philips Allegro/GEMINI PET systems using GATE," Physics in Medicine and Biology, vol. 51, pp. 943-962, 2006] [Brad J. Kemp, Chang Kim, John J. Williams, Alexander Ganin, Val J. Lowe, "NEMA NU 2-2001 performance measurements of an LYSO-based PET/CT system in 2D and 3D acquisition patterns," Journal of Nuclear Medicine, vol. 47, pp. 1960-1967, 2006]; and for the animal PET, the spatial resolution is about 1 mm~2 mm FWHM, the FOV in the vertical axial direction is approximately 10 cm~15 cm, the width of the scintillation crystal in the tangential direction is generally about 1 mm~2 mm [Laforest Richard, Longford Desmond, Siegel Stefan, Newport Danny F., Yap Jeffrey, "Performance evaluation of the microPET-Focus-F120," in IEEE 2004 Nuclear Science Symposium Conference Record, vol. 5, pp. 2965-2969, 2004] [Cristian C Constantinescu, Jogeshwar Mukherjee, "Performance evaluation of an Inveon PET preclinical scanner," Physics in Medicine and Biology, vol. 54, pp. 2885-2899, 2009]. In order to obtain a PET with a spatial resolution the same as or higher than that of the animal PET while maintaining large FOV, it is required to use a large number of crystals with finely cut, and the number of the crystals increases in a multiple proportional to the square of the ratio of the radius of detection ring between the two PETs. With the increase of the number of the crystals, more and faster photomultiplier tubes and a large number of back-end electronics channels would be needed, leading to a sharp increase in the cost of the entire PET system.

SUMMARY OF THE INVENTION

The object of the present invention is to provide a positron emission tomography imaging method and imaging device with application adaptability. The positron emission tomography imaging method can achieve better system performance with a lower system cost, and the corresponding imaging device can improve the system performance by several times to several decuples and obtain images with high quality in a region of interest of an object under detection only by changing the imaging method without increasing the system cost.

The present invention provides a positron emission tomography imaging method with application adaptability, including the following steps:

I. performing an initial scan for obtaining preliminary activity information of an object under detection;

II. according to the result of the initial scan obtained in the step I, programming a performance and a layout of detector blocks and imaging parameters, adjusting the detector blocks so as to obtain a new system structure, and performing a rapid calibration for the new system structure;

III. performing a scan with the new system structure for obtaining activity information of the object under detection; and IV. analyzing the activity information of the object under detection obtained in the step III; finishing the scan in a case that a quality of the activity information satisfies the requirement of the application; and in a case that the quality of the activity information does not satisfy the requirement of the application, re-programming the performance and the layout of the detector blocks and the imaging parameters, adjusting the detector blocks, performing rapid calibration, and repeating the steps III to IV.

Specifically, the step II includes:

a. extracting a location and a size of a region of interest, according to the activity information of the object under detection obtained by the initial scan;

b. programming the performance and the layout of the detector blocks and the imaging parameters, according to the location and the size of the region of interest in conjunction with a characteristic of the object under detection and the imaging performance requirement;

c. adjusting the detector blocks according to the result of the programming, so as to obtain the new system structure; and d. performing a rapid calibration for the new system structure.

An positron emission tomography imaging device with application adaptability provided by the invention includes a detector module, a detector control module, an image reconstruction module and a detector programming module; an output of the detector module is connected with the detector control module, an output of the detector control module is connected with the detector module and the image reconstruction module respectively, an output of the image reconstruction module is connected with the detector programming module, and an output of the detector programming module is connected with the detector control module;

the detector module is adapted to receive and deposit γ photons and includes a plurality of independent detector blocks, with each of the detector blocks having an independent electronic system; and the detector module is further adapted to transmit information of the detector blocks to the detector control module; the information of the detector blocks includes a performance and a layout of the detector blocks and imaging parameters and information of a detected event; the detector control module is adapted to control the detector blocks according to a programmed performance and layout of the detector blocks and imaging parameters received from the detector programming module and transmit the information of the detector blocks to the image reconstruction module; the image reconstruction module is adapted to process the information of the detector blocks obtained from the detector control module; and the detector programming module is adapted to program the performance and the layout of the detector blocks and the imaging parameters and transmit the result of the programming to the detector control module.

A second configuration of an positron emission tomography imaging device with application adaptability provided by the invention includes a detector module, a detector control module, an image reconstruction module and a detector programming module; an output of the detector module is connected with the detector control module and the image reconstruction module respectively, an output of the detector control module is connected with the detector module and the image reconstruction module respectively, an output of the image reconstruction module is connected with the detector programming module, and an output of the detector programming module is connected with the detector control module;

the detector module is adapted to receive and deposit γ photons and includes a plurality of independent detector blocks, with each of the detector blocks having an independent electronic system; and the detector module is further adapted to transmit a performance and a layout of the detector blocks and imaging parameters to the detector control module and transmit information of a detected event to the image reconstruction module; the detector control module is adapted to control the detector blocks according to a programmed performance and layout of the detector blocks and imaging parameters received from the detector programming module and transmit the performance and the layout of the detector blocks and the imaging parameters to the image reconstruction module; the image reconstruction module is adapted to process the performance and the layout of the detector blocks, the imaging parameters and the information of the detected event obtained from the detector module and the detector control module; and the detector programming module is adapted to program the performance and the layout of the detector blocks and the imaging parameters and transmit the result of the programming to the detector control module.

A third configuration of an positron emission tomography imaging device with application adaptability provided by the invention includes a detector module, a detector control module, an image reconstruction module and a detector programming module; an output of the detector module is connected with the image reconstruction module, an output of the detector control module is connected with the detector module, an output of the image reconstruction module is connected with the detector programming module, and an output of the detector programming module is connected with the detector control module;

the detector module is adapted to receive and deposit γ photons and includes a plurality of independent detector blocks, with each of the detector blocks having an independent electronic system; and the detector module is further adapted to transmit information of the detector blocks to the image reconstruction module; the information of the detector blocks includes a performance and a layout of the detector blocks and imaging parameters and information of a detected event; the detector control module is adapted to control the detector blocks according to a programmed performance and layout of the detector blocks and imaging parameters received from the detector programming module and transmit the performance and the layout of the detector blocks and the imaging parameters to the detector module; the image reconstruction module is adapted to process the information of the detector blocks obtained from detector module; and the detector programming module is adapted to program the performance and the layout of the detector blocks and the imaging parameters.

The advantages of the invention are as follows. Compared with the system which completely utilizes detector blocks with high performance, a same or comparable image quality can be obtained in the region of interest of the object under detection by utilizing a system including a certain number of detector blocks with high performance, and thereby the system cost is reduced.

| 1—detector module | 2—detector control module |
|---|---|
| 3—image reconstruction module | 4—detector programming module |

DETAILED DESCRIPTION OF THE INVENTION

The invention will be described further in detail in conjunction with the accompany drawings and embodiments as follows.

Figure 1:
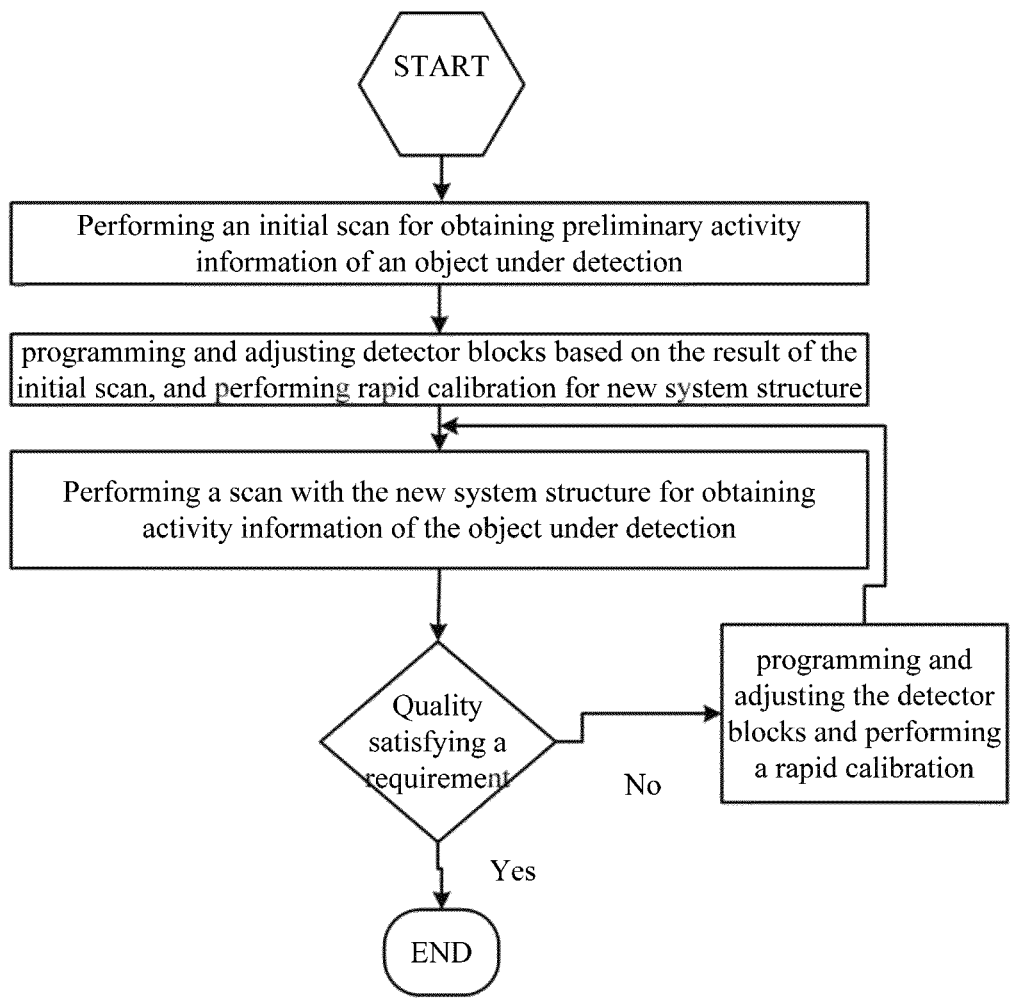
FIG. 1 is a flow chart of a positron emission tomography imaging method with application adaptability according to the invention.

As shown in FIG. 1, a positron emission tomography imaging method with application adaptability according to the invention is as follows.

(1) An initial scan is performed for obtaining preliminary activity information of an object under detection;

Detector blocks are programmed to be in a layout of surrounding the object under detection, according to a structural characteristic, an imaging characteristic and an imaging performance requirement of the object under detection and based on the performance and geometrical dimensions of the detector blocks in an imaging system; a detecting ring with a regular geometric shape, such as a circular shape or an elliptical shape, may be utilized; alternatively, a detecting ring with an irregular convex shape may be utilized; alternatively, a detecting ring with a geometric shape similar to the object under detection may be utilized according to the structural characteristic of the object under detection. For example, the detecting ring is in a shape similar to the mammary for a mammary scan. Each of the detector blocks on the detecting ring surrounding the object under detection may has different performance and imaging parameters.

An attenuation correction may be performed by CT or a rod source or a spectrum when obtaining the activity information of the object under detection. [Paul E. Kinahan, Bruce H. Hasegawa, Thomas Beyer, "X-ray-based attenuation correction for positron emission tomography/computed tomography scanners," Seminars in Nuclear Medicine, vol. 33, pp. 166-179, 2003]

An analytic or iterative reconstruction may be used for an image reconstruction, including FBP (Filtered Back Projection), MLEM (Maximum Likelihood Expectation Maximization), OSEM (Ordered Subset Expectation Maximum) and MAP (Maximum a Posteriori). [Andrew J. Reader, Habib Zaidi, "Advances in PET Image Reconstruction," Clin., pp. 173-190, 2007]

(2) According to the result of the initial scan obtained in the step (1), the performance and the layout of the detector blocks and the imaging parameters are programmed, the detector blocks are adjusted so as to obtain a new system structure, and the new system structure is rapidly corrected. The step (2) includes:

(2.1) A location and a size of a region of interest are extracted according to the activity information of the object under detection obtained by the initial scan. The location and the size of the region of interest may be extracted manually, semi-automatically or fully automatically.

[Dewalle-Vignion A S, E I Abiad A, Betrouni N, Hossein-Foucher C, Huglo D, Vermandel M, "Thresholding methods for PET imaging: A review," Medicine Nucleaire, vol. 34, no. 2, pp. 119-131, 2010]

(2.2) The performance and the layout of the detector blocks and the imaging parameters are programmed, according to the location and the size of the region of interest in conjunction with a characteristic of the object under detection and the imaging performance requirement. Parameters for the performance of the detector blocks include an intrinsic spatial resolution, a timing resolution, an energy resolution, sensitivity and a counting rate; and the imaging parameters include a detector parameter, an electronic parameter and an image reconstruction parameter. Each of detector blocks on the detecting ring surrounding the object under detection may have different performance and imaging parameters.

The programming of the layout of the detector blocks includes programming the detector blocks to be in a layout of surrounding the object under detection, according to the location and the size of the region of interest, a structural characteristic and an imaging characteristic of the object under detection and the required performance of the imaging and based on the performance and the geometrical dimensions of the detector blocks in the imaging system. Moreover, a detecting ring with a regular geometric shape, such as a circular shape or an elliptical shape, may be utilized; alternatively, a detecting ring with an irregular convex shape may be utilized; alternatively, a detecting ring with a geometric shape similar to the object under detection may be utilized according to the structural characteristic of the object under detection. For example, the detecting ring is in a shape similar to the mammary when being used for a mammary scan.

(i) Layout of the detector blocks

The detector blocks may form a detecting ring to surround the object under detection in the transaxial slices and may be arranged in a panel mode. The panel mode means that the detecting planes of two or more detector blocks are coplanar and the detecting planes of two adjacent detector blocks have one overlapped edge. There may be the following layout patterns:

(2.2.1) The detector blocks are distributed on a detecting ring in an equally spaced way. The size of the detecting ring may be adjusted according to the locations and sizes of the object under detection, the detected part and the region of interest.

(2.2.2) The detector blocks are distributed on a detecting ring in a manner that, sections of detector blocks are clustered into a single aggregation or multiple aggregations.

(2.2.2.1) The single aggregation of the detector blocks may have a layout as follows:

A) All of the detector blocks are aggregated near the region of interest.

B) Some of the detector blocks are aggregated near the region of interest and the remaining of the detector blocks may be distributed on the remaining portion of the detecting ring in an equally spaced way.

(2.2.2.2) The multiple aggregations of the detector blocks may be distributed on the detecting ring in a variety of symmetric patterns, in which each of the symmetric aggregations of the detector blocks may have different number of the detector blocks. The symmetry is implemented with taking the center of the aggregated detector blocks on the transect as a reference point. The patterns for the symmetry include:

A) a symmetry with respect to a certain center;

B) a symmetry with respect to a symmetry axis which is a straight line through a certain center, and the symmetry axis may be:

(a) a straight line defined by the reference point of a aggregated or un-aggregated detector module and the center, or (b) a straight line defined by two centers, in which the center is a center of the detecting ring, or a center of the region of interest, or a center of a portion region of the region of interest, or a center of the object under detection. The center may be a geometric center or a center of gravity.

C) a symmetry with respect to a line connecting reference points of two aggregated or un-aggregated detector blocks or reference points of one aggregated detector module and one un-aggregated detector module.

(ii) Parameters of the detector block include a supply voltage of the detector block, the position spectral correction parameters, the normalization correction parameters, the photomultiplier gain correction parameters and so on.

(iii) Electronic parameters include the voltage thresholds, the time windows, the energy windows, the dead time correction parameters, the baseline correction parameters, the global clock correction parameters and so on.

(iv) Image reconstruction parameters include the system response matrix, the event information screening criterions and so on.

(2.3) The detector blocks are adjusted according to the result of the programming, so as to obtain the new system structure;

(2.4) The new system is rapidly calibrated (in the invention "correction/correct" and "calibration/calibrate" are interchangeable). Compensation and optimization performed in the image and system level includes the normalized correction, the dead time correction, the random correction, the scatter correction and so on; compensation and optimization performed in the detector and electronic level includes the photomultiplier tubes' gain calibration, the location calibration, the energy calibration, the time calibration, the baseline drift calibration, the global clock calibration and so on.

(3) a scan is performed with the new system structure for obtaining activity information of the object under detection.

When the activity information of the object under detection is obtained, the activity information obtained by the initial scan in the step (1) may be used as priori information, or the activity information obtained with a preceding system structure or a certain previous system structure may be used as priori information, or the activity information obtained with multiple system structures may be used in combination as the priori information, and then an image reconstruction is performed with the new layout by utilizing the priori information.

Reference is made to step (1) for the attenuation correction method and the image reconstruction method.

(4) The activity information of the object under detection obtained in the step (3) is analyzed. If quality of the activity information satisfies a requirement of the application, the scan is finished; otherwise, the performance and the layout of the detector blocks and the imaging parameters are re-programmed, the detector blocks are adjusted, the rapid correction is performed, and the steps (3) to (4) are repeated.

When the parameters of the detector module is re-programmed, the result of the initial scan obtained in the step (1) or the result of the scan obtained by performing the step (3) for once or multiple times may be utilized, or both the scan result obtained in the step (1) and the scan result obtained by performing the step (3) for once or multiple times may be utilized.

The analyzed quality parameters include a spatial resolution, sensitivity, a signal-to-noise ratio, a contrast and/or a user defined metric. [National Electrical Manufacturers Association, NEMA Standards Publication NU 2-2007, Performance Measurements Of Small Animal Positron Emission Tomographs, 2007]

Reference is made to the step (2) for the programming method, the adjustment of the detector module's parameters and the quick calibration.

Figure 2A:
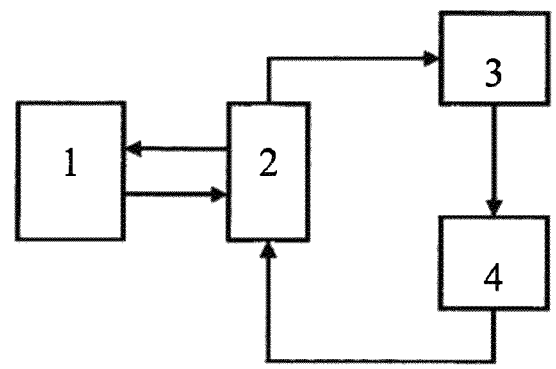
FIG. 2 is a schematic structural view of a positron emission tomography imaging device with application adaptability according to the invention.
Figure 2B:
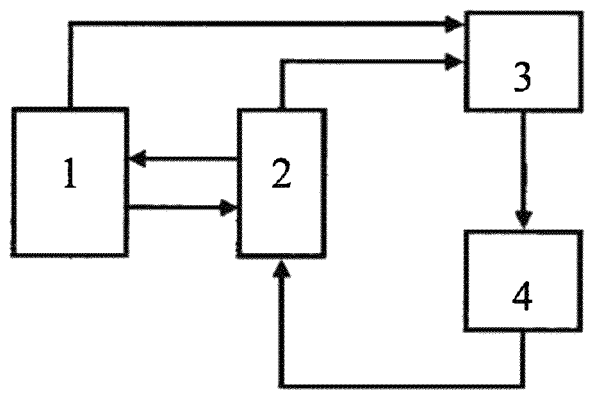
Figure 2C:
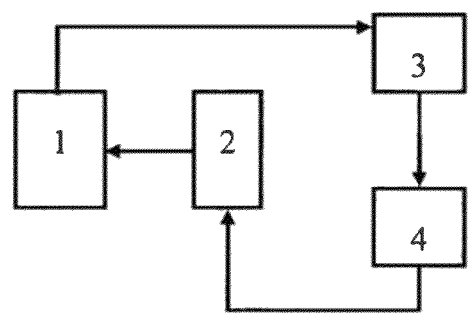

As shown in FIG. 2, a positron emission tomography imaging device with application adaptability according to the invention includes a detector module 1, a detector control module 2, an image reconstruction module 3 and a detector programming module 4. There are three configurations.

A first configuration is shown in FIG. 2(a), in which an output of the detector module 1 is connected with the detector control module 2, an output of the detector control module 2 is connected with the detector module 1 and the image reconstruction module 3 respectively, an output of the image reconstruction module 3 is connected with the detector programming module 4, and an output of the detector programming module 4 is connected with the detector control module 2;

(A) the detector module 1 is adapted to receive and deposit γ photons and includes multiple independent detector blocks, with each of the detector blocks having an independent electronic system and being able to move in multiple degrees of freedom; and the detector module 1 is further adapted to transmit information of the detector blocks to the detector control module 2; the information of the detector component includes performance, a layout, an imaging parameter of the detector component and information of a detected event;

(B) the detector control module 2 is adapted to control the detector blocks according to programmed performance and layout of the detector blocks and imaging parameters received from the detector programming module 4 and transmit the information of the detector blocks to the image reconstruction module 3;

(C) the image reconstruction module 3 is adapted to process the information of the detector blocks obtained from the detector control module 2, so as to obtain activity information of an object under detection; and (D) the detector programming module 4 is adapted to program the performance and the layout of the detector blocks and the imaging parameters and transmit the result of the programming to the detector control module 2.

A second configuration is shown in FIG. 2(b), in which an output of the detector module 1 is connected with the detector control module 2 and the image reconstruction module 3 respectively, an output of the detector control module 2 is connected with the detector module 1 and the image reconstruction module 3 respectively, an output of the image reconstruction module 3 is connected with the detector programming module 4, and an output of the detector programming module 4 is connected with the detector control module 2;

(A) the detector module 1 is adapted to receive and deposit γ photons and includes multiple independent detector blocks, with each of the detector blocks having an independent electronic system and being able to move in multiple degrees of freedom; and the detector module 1 is further adapted to transmit performance, a layout, an imaging parameters of the detector blocks to the detector control module 2 and transmit information of a detected event to the image reconstruction module 3;

(B) the detector control module 2 is adapted to control the detector blocks according to programmed performance and layout of the detector blocks and imaging parameters received from the detector programming module 4 and transmit the performance and the layout of the detector blocks and the imaging parameters to the image reconstruction module 3;

(C) the image reconstruction module 3 is adapted to process the performance and the layout of the detector blocks, the imaging parameters and the information of the detected event obtained from the detector module 1 and the detector control module 2, so as to obtain activity information of an object under detection; and (D) the detector programming module 4 is adapted to program the performance and the layout of the detector blocks and the imaging parameters and transmit the result of the programming to the detector control module 2.

A third configuration is shown in FIG. 2(*c*), in which an output of the detector module 1 is connected with the image reconstruction module 3, an output of the detector control module 2 is connected with the detector module 1, an output of the image reconstruction module 3 is connected with the detector programming module 4, and an output of the detector programming module 4 is connected with the detector control module 2;

(A) the detector module 1 is adapted to receive and deposit γ photons and includes multiple independent detector blocks, with each of the detector blocks having an independent electronic system and being able to move in multiple degrees of freedom; and the detector module 1 is further adapted to transmit information of the detector blocks to the image reconstruction module 3; the information of the detector blocks includes performance, layout, imaging parameters of the detector blocks and information of a detected event;

(B) the detector control module 2 is adapted to control the detector blocks according to programmed performance, layout and imaging parameters of detector blocks received from the detector programming module 4 and transmit the performance and the layout of the detector blocks and the imaging parameters to the detector module 1;

(C) the image reconstruction module 3 is adapted to process the information of the detector blocks obtained from detector module 1, so as to obtain activity information of an object under detection; and (D) the detector programming module 4 is adapted to program the performance and the layout of the detector blocks and the imaging parameters and transmit the result of the programming to the detector control module 2.

Example

Figure 3:
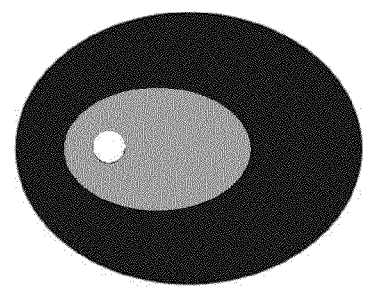
FIG. 3 is a simulated object under detection in the invention.

The embodiment of the invention will be described further in detail as follows by taking a simulated object under detection shown in FIG. 3 as an example. In FIG. 3, a white region represents a region of interest, a gray region represents an organ/tissue where the region of interest located, and the darkest region represents other organs/tissues in the transect of the object under detection.

Figure 4:
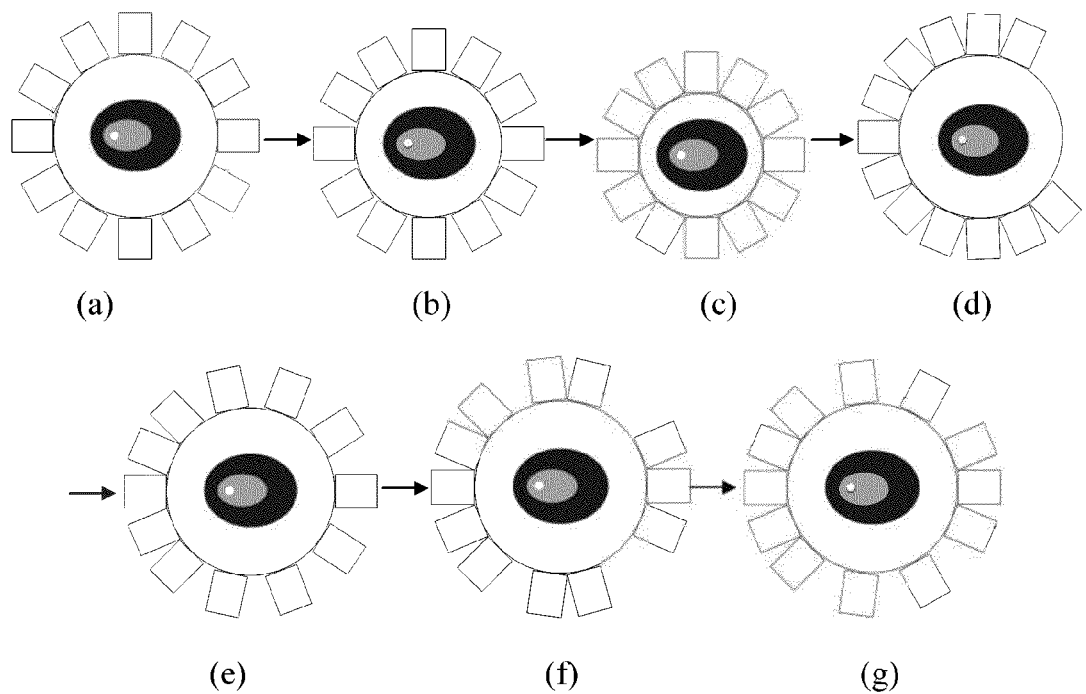
FIG. 4 shows diagrams of the layout of detector blocks in a system according to an embodiment of the invention.

FIG. 4 shows diagrams of layout of detector blocks of a system when an imaging is performed on the simulated object under detection shown in FIG. 3.

In a step (1), during an initial scan, a detection is performed in such a way that the detector blocks are distributed on a regular circular detecting ring in an equally spaced way as shown in FIG. 4(*a*).

FIGS. 4(*b*)-4(*g*) show system structures with different geometries programmed by the detector programming module. Specifically, (b) the radius of the detecting system is changed and the detector blocks are distributed on a circular detecting ring in an equally spaced way; (c) the radius of the detecting system is changed and the detector blocks are distributed on a circular detecting ring without any space between each other; (d) all of the detector blocks are clustered into an aggregation near the region of interest; (e) some of the detector blocks are clustered into an aggregation near the region of interest and the others of the detector blocks are distributed on a circular detecting ring in an equally spaced way; (f) some of the detector blocks are distributed symmetrically with respect to a center of a circular detecting ring, in the figure, five aggregated blocks on the left and three aggregated blocks on the right are symmetric with respect to the center of the circular detecting ring, two adjoining upper detector blocks and two adjoining lower detector blocks are symmetric both with respect to a connection line defined by the five aggregated blocks on the left and the region of interest and with respect to a connection line defined by a reference point of the five aggregated blocks on the left and a reference point of three aggregated blocks on the right; (g) some of the detector blocks are distributed symmetrically with respect to a center of a circular detecting ring, in the figure, five aggregated blocks on the left and three aggregated blocks on the right are symmetric with respect to the center of the circular detecting ring, and the others of the detector blocks are distributed on the circular detecting ring in an equally spaced way.

In the embodiment, each of the detector blocks shown in the figure may be in a panel mode and may have different sizes. The detecting ring may be a detecting ring with another regular shape, or may be a detecting ring with an irregular convex shape, or may be a detecting ring with a geometric shape similar to an object under detection.

The examples described above are only exemplary embodiments of the invention and do not represent the result of the programming by an actual detector programming module. Moreover, the invention is not limited by the content disclosed by the examples and the accompany drawings. Therefore, any equivalent or modification made without departing from the spirit of the disclosure falls within the scope of protection of the invention.

The invention discloses a positron emission tomography imaging method and imaging device with application adaptability. In the positron emission tomography imaging method, an initial scan is firstly performed for obtaining preliminary activity information; according to the result of the initial scan, detector blocks are programmed and adjusted so as to obtain a new system structure, and the new system structure is rapidly corrected; a scan is performed with the new system structure for obtaining activity information of the object under detection, if quality of the activity information satisfies a requirement of the application, the scan is finished, otherwise, the detector blocks are re-programmed and adjusted, the rapid correction is performed, and the activity information of the object wider detection is obtained again with another new system structure until the quality of the activity information satisfies the requirement of the application. The positron emission tomography imaging device includes a detector module, a detector control module, an image reconstruction module and a detector programming module. The positron emission tomography imaging method can achieve better system performance with a lower system cost, and improve the system performance by several times to several decuples, save the system cost and obtain images with high quality in a region of interest of the object under detection.

The invention claimed is:

1. A positron emission tomography imaging method with application adaptability, comprising the following steps:
   - step I, performing an initial scan for obtaining preliminary activity information of an object under detection;
   - step II, according to a result of the initial scan obtained in the step I, programming a performance and a layout of detector blocks and imaging parameters, adjusting the detector blocks so as to obtain a new system structure, and performing a rapid calibration for the new system structure;
   - step III, performing a scan with the new system structure for obtaining activity information of the object under detection; and
   - step IV, analyzing the activity information of the object under detection obtained in the step III; finishing the scan in a case that a quality of the activity information satisfies a requirement of the application; and in a case that the quality of the activity information does not satisfy the requirement of the application, re-programming the performance and the layout of the detector blocks and the imaging parameters, adjusting the detector blocks, performing rapid calibration; and
   - step V, repeating the steps III to IV.

2. The positron emission tomography imaging method with application adaptability according to claim 1, wherein performing the initial scan in the step 1 comprises programming the detector blocks to be in a layout of surrounding the object under detection, according to a structural characteristic, an imaging characteristic and an imaging performance requirement of the object under detection and based on the performance and geometrical dimensions of the detector blocks in an imaging system.

3. The positron emission tomography imaging method with application adaptability according to claim 2, wherein the layout of surrounding utilizes a detecting ring with a regular geometric shape, or utilizes a detecting ring with an irregular convex shape, or utilizes a detecting ring with a geometric shape similar to the object under detection according to the structural characteristic of the object under detection.

4. The positron emission tomography imaging method with application adaptability according to claim 1, wherein the step II comprises:
   - step a, extracting a location and a size of a region of interest, according to the activity information of the object under detection obtained by the initial scan;
   - step b, programming the performance and the layout of the detector blocks and the imaging parameters, according to the location and the size of the region of interest in conjunction with a characteristic of the object under detection and the imaging performance requirement;
   - step c, adjusting the detector blocks according to a result of the programming, so as to obtain the new system structure; and
   - step d, performing a rapid calibration for the new system structure.

5. The positron emission tomography imaging method with application adaptability according to claim 4, wherein the location and the size of the region of interest are extracted manually, semi-automatically or fully automatically in the step a.

6. The positron emission tomography imaging method with application adaptability according to claim 4, wherein, in the step b, the performance of the detector blocks comprises an intrinsic spatial resolution, a timing resolution, an energy resolution, sensitivity and a counting rate; and the imaging parameters comprise a detector parameter, an electronic parameter and an image reconstruction parameter.

7. The positron emission tomography imaging method with application adaptability according to claim 4, wherein programming the layout of the detector blocks in the step b comprises programming the detector blocks to be in a layout of surrounding the object under detection, according to the location and the size of the region of interest, a structural characteristic and an imaging characteristic of the object under detection and the performance requirement of the imaging and based on the performance and geometrical dimensions of the detector blocks in an imaging system.

8. The positron emission tomography imaging method with application adaptability according to claim 7, wherein the layout of surrounding utilizes a detecting ring with a regular geometric shape, or utilizes a detecting ring with an irregular convex shape, or utilizes a detecting ring with a geometric shape similar to the object under detection according to the structural characteristic of the object under detection.

9. The positron emission tomography imaging method with application adaptability according to claim 7, wherein the detector blocks are distributed on a detecting ring in an equally spaced way.

10. The positron emission tomography imaging method with application adaptability according to claim 7, wherein the detector blocks are distributed on a detecting ring in a manner that, sections of detector blocks are clustered into a single aggregation or a plurality of aggregations.

11. The positron emission tomography imaging method with application adaptability according to claim 10, wherein the plurality of aggregations of the detector blocks are distributed on the detecting ring in a variety of symmetric patterns.

12. The positron emission tomography imaging method with application adaptability according to claim 11, wherein symmetric aggregations of the detector blocks have different numbers of the detector blocks.

13. The positron emission tomography imaging method with application adaptability according to claim 11, wherein the symmetric pattern is a symmetry with respect to a certain center, or a symmetry with respect to a symmetry axis which is a straight line through a certain center, wherein the symmetry axis is an axis defined by an aggregated or un-aggregated detector module and the center or an axis defined by two centers, the center is a center of the detecting ring, or a center of the region of interest, or a center of a portion region of the region of interest, or a center of the object under detection, and wherein the center is a geometric center or a center of gravity.

14. The positron emission tomography imaging method with application adaptability according to claim 11, wherein the symmetric pattern is a symmetry with respect to a line connecting reference points of two aggregated detector blocks or reference points of two un-aggregated detector blocks or reference points of one aggregated detector module and one un-aggregated detector module.

15. The positron emission tomography imaging method with application adaptability according to claim 10, wherein the single aggregation of the detector blocks is distributed on the detecting ring such that all of the detector blocks are aggregated near the region of interest; or some of the detector blocks are aggregated near the region of interest and the remaining of the detector blocks are distributed on the remaining portion of the detecting ring in an equally spaced way.

16. The positron emission tomography imaging method with application adaptability according to claim 1, wherein an attenuation correction is performed by a CT or a rod source or an atlas during obtaining the activity information of the object under detection in the step I and the step III.

17. The positron emission tomography imaging method with application adaptability according to claim 1, wherein, during obtaining the activity information of the object under detection in the step III, the activity information obtained by the initial scan in the step I is used as priori information, or the activity information obtained with a preceding system structure or a certain previous system structure is used as a priori information, or the activity information obtained with multiple system structures is used in combination as the priori information, and then an image reconstruction is performed with a new layout by utilizing the priori information.

18. The positron emission tomography imaging method with application adaptability according to claim 1, wherein re-programming the performance and the layout of the detector blocks and the imaging parameters in the step IV is performed by utilizing the result of the initial scan obtained in the step I or the result of the scan obtained by performing the step III for once or multiple times, or utilizing both the result of the initial scan obtained in the step I and the result of the scan obtained by performing the step III for once or multiple times.

19. The positron emission tomography imaging method with application adaptability according to claim 1, wherein the quality of the activity information of the object under detection is analyzed in the step IV, wherein the quality is one or more of a spatial resolution, sensitivity, a signal-to-noise ratio, a contrast or a metric defined by users.

20. A positron emission tomography imaging device, comprising a detector module, a detector control module, an image reconstruction module and a detector programming module, wherein:
an output of the detector module is connected with the detector control module, an output of the detector control module is connected with the detector module and the image reconstruction module respectively, an output of the image reconstruction module is connected with the detector programming module, and an output of the detector programming module is connected with the detector control module;
the detector module is configured to receive and deposit γ photons and comprises a plurality of independent detector blocks, with each of the detector blocks having an independent electronic system; and the detector module is further configured to transmit information of the detector blocks to the detector control module; the information of the detector blocks comprises a performance and a layout of the detector blocks and imaging parameters and information of a detected event;
the detector control module is configured to control the detector blocks according to a programmed performance and a layout of the detector blocks and imaging parameters received from the detector programming module and transmit the information of the detector blocks to the image reconstruction module;
the image reconstruction module is configured to process the information of the detector blocks obtained from the detector control module; and
the detector programming module is configured to program the performance and the layout of the detector blocks and the imaging parameters and transmit a result of the programming to the detector control module.

21. A positron emission tomography imaging device, comprising a detector module, a detector control module, an image reconstruction module and a detector programming module, wherein:
an output of the detector module is connected with the detector control module and the image reconstruction module respectively, an output of the detector control module is connected with the detector module and the image reconstruction module respectively, an output of the image reconstruction module is connected with the detector programming module, and an output of the detector programming module is connected with the detector control module;
the detector module is configured to receive and deposit γ photons and comprises a plurality of independent detector blocks, with each of the detector blocks having an independent electronic system; and the detector module is further configured to transmit a performance and a layout of the detector blocks and imaging parameters to the detector control module and transmit information of a detected event to the image reconstruction module;
the detector control module is configured to control the detector blocks according to a programmed performance and layout of the detector blocks and imaging parameters received from the detector programming module and transmit the performance and the layout of the detector blocks and the imaging parameters to the image reconstruction module;
the image reconstruction module is configured to process the performance and the layout of the detector blocks, the imaging parameters and the information of the detected event obtained from the detector module and the detector control module; and
the detector programming module is configured to program the performance and the layout of the detector blocks and the imaging parameters and transmit a result of the programming to the detector control module.

22. A positron emission tomography imaging device, comprising a detector module, a detector control module, an image reconstruction module and a detector programming module, wherein:
an output of the detector module is connected with the image reconstruction module, an output of the detector control module is connected with the detector module, an output of the image reconstruction module is connected with the detector programming module, and an output of the detector programming module is connected with the detector control module;
the detector module is configured to receive and deposit γ photons and comprises a plurality of independent detector blocks, with each of the detector blocks having an independent electronic system; and the detector module is further configured to transmit information of the detector blocks to the image reconstruction module; the information of the detector blocks comprises a performance and a layout of the detector blocks and imaging parameters and information of a detected event;

the detector control module is configured to control the detector blocks according to a programmed performance, a layout and imaging parameters of the detector blocks received from the detector programming module and transmit the performance and the layout of the detector blocks and the imaging parameters to the detector module;

the image reconstruction module is configured to process the information of the detector blocks obtained from the detector module; and the detector programming module is configured to program the performance and the layout of the detector blocks and the imaging parameters.

* * * * *